United States Patent
Putila et al.

(10) Patent No.: US 10,064,581 B2
(45) Date of Patent: Sep. 4, 2018

(54) ENHANCING PHYSICAL ACTIVITY MEASUREMENT

(71) Applicant: Polar Electro Oy, Kempele (FI)

(72) Inventors: Veli-Pekka Putila, Oulu (FI); Kaisa Lamsa, Oulu (FI); Lauri Lumme, Oulu (FI); Olli Komulainen, Oulu (FI); Ville Majava, Kiviniemi (FI); Risto Kuusela, Oulu (FI); Arto Niva, Jaali (FI)

(73) Assignee: Polar Electro Oy, Kempele (FI)

( * ) Notice: Subject to any disclaimer, the term of this patent is extended or adjusted under 35 U.S.C. 154(b) by 604 days.

(21) Appl. No.: 14/681,642

(22) Filed: Apr. 8, 2015

(65) Prior Publication Data

US 2016/0296170 A1 Oct. 13, 2016

(51) Int. Cl.

| | |
|---|---|
| A61B 5/04 | (2006.01) |
| A61B 5/00 | (2006.01) |
| A61B 5/024 | (2006.01) |
| A61B 5/0245 | (2006.01) |
| A61B 5/0408 | (2006.01) |
| A61B 5/11 | (2006.01) |

(52) U.S. Cl.
CPC .......... *A61B 5/6831* (2013.01); *A61B 5/0245* (2013.01); *A61B 5/02438* (2013.01); *A61B 5/02444* (2013.01); *A61B 5/04085* (2013.01); *A61B 5/1118* (2013.01); *A61B 2562/0209* (2013.01); *A61B 2562/125* (2013.01); *A61B 2562/164* (2013.01)

(58) Field of Classification Search
CPC . A61B 5/04085; A61B 5/0006; A61B 5/6804; A61B 5/6831; A61B 5/6833; A61B 2560/0412; A61B 5/0205; A61B 5/6823; A61B 5/053; A61B 5/0531; A61B 2562/0219; A61B 5/024

USPC .............. 600/382, 384, 386, 388, 393, 390
See application file for complete search history.

(56) References Cited

U.S. PATENT DOCUMENTS

| | | | |
|---|---|---|---|
| 4,248,247 A | 2/1981 | Ware et al. | |
| 6,580,943 B2 * | 6/2003 | Nissila | A61B 5/0006 600/372 |
| 2010/0049028 A1 * | 2/2010 | Shin | A61B 5/0416 600/391 |
| 2011/0028822 A1 * | 2/2011 | Beck | A61B 5/0408 600/386 |
| 2011/0172549 A1 * | 7/2011 | Wijesiriwardana | A61B 5/02438 600/509 |
| 2012/0089037 A1 | 4/2012 | Bishay et al. | |

(Continued)

FOREIGN PATENT DOCUMENTS

EP 1 166 713 A1 6/2001

OTHER PUBLICATIONS

International Search Report, Application No. PCT/EP2016/056516, dated May 24, 2016.

*Primary Examiner* — Joseph Stoklosa
*Assistant Examiner* — Brian M Antiskay
(74) *Attorney, Agent, or Firm* — FisherBroyles, LLP

(57) ABSTRACT

An electrode belt includes at least one electrode to measure biometric signals related to heart activity of a user, a non-conductive strip having at least one opening, and a flexible strip to enable placement of the electrode belt against the skin of the user. The non-conductive strip is coupled with the flexible strip such that, when in use, the at least one electrode is in physical contact with the skin of the user.

18 Claims, 8 Drawing Sheets

(56) References Cited

U.S. PATENT DOCUMENTS

| | | |
|---|---|---|
| 2013/0131460 A1 | 5/2013 | Yuen |
| 2013/0131484 A1 | 5/2013 | Pernu et al. |
| 2014/0088397 A1* | 3/2014 | Chon .................... A61B 5/0424 600/384 |
| 2014/0275852 A1 | 9/2014 | Hong et al. |
| 2014/0336493 A1* | 11/2014 | Kulach .............. A61B 5/04085 600/390 |
| 2016/0007919 A1* | 1/2016 | Pernu .................... A61B 5/6804 600/388 |

* cited by examiner

352 PROVIDING AT LEAST ONE ELECTRODE TO MEASURE BIOMETRIC SIGNALS RELATED TO HEART ACTIVITY OF A USER

354 PROVIDING A NON-CONDUCTIVE STRIP HAVING AT LEAST ONE OPENING

356 APPLYING THE AT LEAST ONE ELECTRODE ON THE NON-CONDUCTIVE STRIP

358 FOLDING AT LEAST TWO PORTIONS OF THE NON-CONDUCTIVE STRIP AGAINST EACH OTHER, WHEREIN THE AT LEAST ONE ELECTRODE IS POSITIONED BETWEEN THE FOLDED AT LEAST TWO PORTIONS OF THE NON-CONDUCTIVE STRIP SO THAT THE AT LEAST ONE ELECTRODE IS ENABLED TO BE IN PHYSICAL CONTACT WITH A SKIN OF THE USER THROUGH THE AT LEAST ONE OPENING

360 PROVIDING A FLEXIBLE STRIP TO ENABLE PLACEMENT OF THE ELECTRODE BELT AGAINST THE SKIN OF THE USER

362 COUPLING THE NON-CONDUCTIVE STRIP TO THE FLEXIBLE STRIP SUCH THAT, WHEN IN USE, THE AT LEAST ONE ELECTRODE IS IN PHYSICAL CONTACT WITH THE SKIN OF THE USER

Fig. 3C

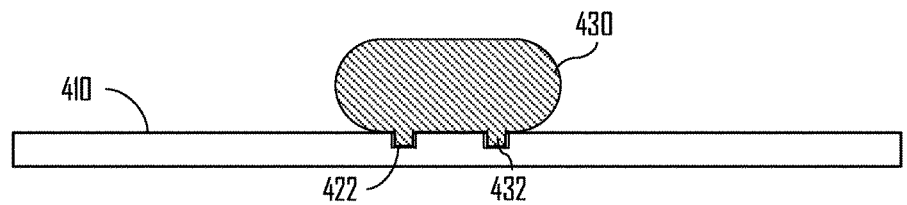
Fig. 4D
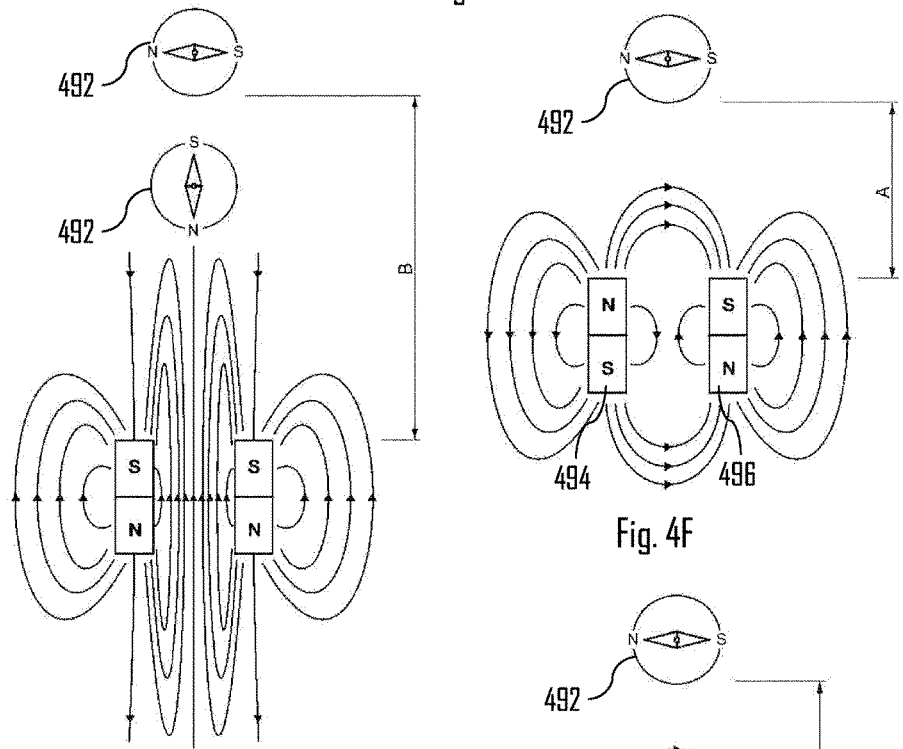
Fig. 4E
Fig. 4F
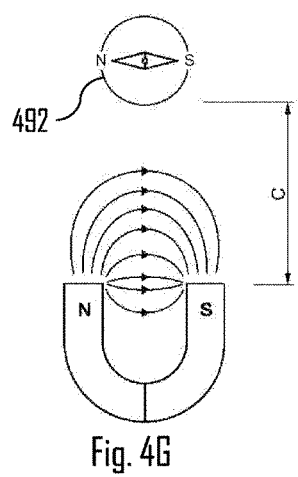
Fig. 4G

ENHANCING PHYSICAL ACTIVITY MEASUREMENT

BACKGROUND

Field

This invention relates to physical activity measurement.

Description of the Related Art

Monitoring physical activity, such as heart rate, has become more and more popular among exercisers. Solutions enhancing the physical activity measurement may be beneficial for a manufacturer to differentiate from competitors. Further, solutions simplifying manufacturing of physical activity measurement devices may be beneficial for the manufacturer.

SUMMARY

According to an aspect, there is provided an electrode belt comprising: at least one electrode to measure biometric signals related to heart activity of a user; a non-conductive strip having at least one opening, wherein the non-conductive strip comprises at least one fold such that at least two portions of the non-conductive strip are folded against each other, wherein a direction of the at least one fold is diverging compared to a longitudinal axis of the non-conductive strip, and wherein the at least one electrode is positioned between the folded at least two portions of the non-conductive strip so that the at least one electrode is enabled to be in physical contact with a skin of the user through the at least one opening; and a flexible strip to enable placement of the electrode belt against the skin of the user, wherein the non-conductive strip is coupled with the flexible strip such that, when in use, the at least one electrode is in physical contact with the skin of the user.

According to an aspect, there is provided a method for manufacturing an electrode belt, the method comprising: providing at least one electrode to measure biometric signals related to heart activity of a user; providing a non-conductive strip having at least one opening; applying the at least one electrode on the non-conductive strip; folding at least two portions of the non-conductive strip against each other, wherein the folding is performed to a direction that is divergent compared to a longitudinal axis of the non-conductive strip, and wherein the at least one electrode is positioned between the folded at least two portions of the non-conductive strip so that the at least one electrode is enabled to be in physical contact with a skin of the user through the at least one opening; providing a flexible strip to enable placement of the electrode belt against the skin of the user; and coupling the non-conductive strip to the flexible strip such that, when in use, the at least one electrode is in physical contact with the skin of the user.

Some embodiments are defined in the dependent claims.

One or more examples of implementations are set forth in more detail in the accompanying drawings and the description below. Other features will be apparent from the description and drawings, and from the claims.

BRIEF DESCRIPTION OF DRAWINGS

In the following embodiments will be described in greater detail with reference to the attached drawings, in which

FIG. 3C illustrates a block diagram according to an embodiment of the invention;

FIGS. 4A to 4G illustrate some embodiments of the invention;

DETAILED DESCRIPTION

The following embodiments are exemplifying. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

Figure 1:
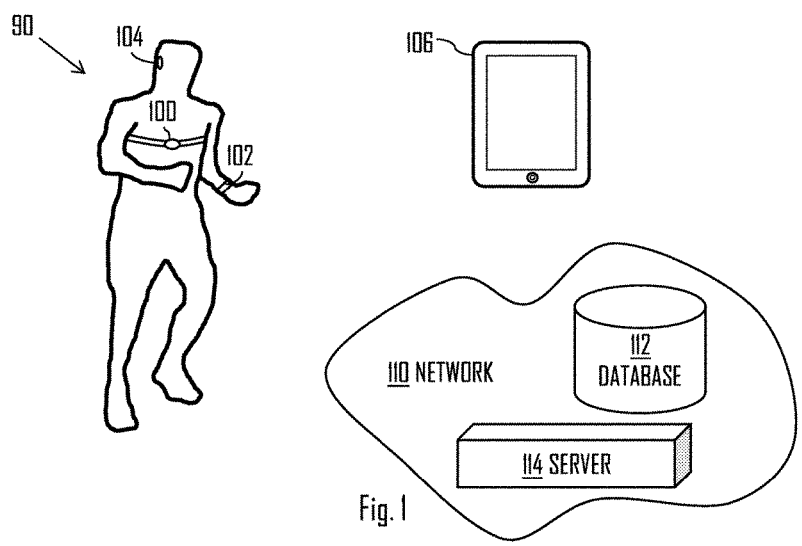
FIG. 1 illustrates a physical activity measurement scenario to which embodiments of the invention may be applied.

FIG. 1 illustrates a physical activity measurement scenario to which embodiments of the invention may be applied. Referring to FIG. 1, for example, heart activity of a user 90 may be monitored by the user 90 using an activity tracker apparatus 102. The activity tracker apparatus 102 may be a portable or wearable electronic device, such as a wrist device 102. The wrist device 102 may comprise a heart activity circuitry configured to determine user's 90 heart activity, such as heart rate for example. The heart activity circuitry may comprise an optical heart activity sensor, such as a PPG (photoplethysmography) sensor, configured to measure heart activity of the user 90. The optical heart activity sensor may detect the user's 90 heart activity by optical heart rate measurement, which may comprise sending a light beam towards body tissue of the user, and measuring the bounced and/or emitted light from the body tissue of the user 90. The body tissue of the user 90 may be, for example, skin of the user 90. The light beam may alter when travelling through the user's 90 veins and the alterations may be detected by the optical heart rate activity sensor. By using the detected data, the wrist device 102, may determine user's 90 heart activity, such as heart rate for example.

The heart activity circuitry may comprise a bioimpedance sensor, wherein the bioimpedance sensor is configured to measure user's 90 heart activity. The bioimpedance measurement may be based on transmitting a radio signal into skin of the user 90, and observing changes in the radio signal due to impedance changes caused by, for example, blood volume changes. Thus, the user's 90 heart activity, such as heart rate, may be determined by the heart activity circuitry from the data produced by the bioimpedance sensor.

Further, besides these types of heart activity sensors, also other types of biosignal measurement sensors may be embedded into the heart activity circuitry. These types include but are not limited to the following: a Laser Doppler-based blood flow sensor, a magnetic blood flow sensor, an Electromechanical Film (EMFi) pulse sensor, a polarization blood flow sensor.

The wrist device 102 may comprise a motion circuitry configured to measure motion of the wrist device 102, wherein the motion circuitry may comprise one or more motion sensor(s). The motion circuitry may be configured to measure the motion of the wrist device 102 in relation to the body tissue of the user 90. Thus, the motion circuitry may provide information about the connection of the wrist device 102 to the wrist of the user 90.

Further, the motion circuitry may be configured to detect motion induced by the user 90 to the wrist device 102 by moving hand in which the user 90 wears the wrist device 102. The motion circuitry may use other motion data, such as location data of the user, to determine user's 90 motion.

In an embodiment, the motion sensor(s) comprise at least one of the following: an accelerometer, a magnetometer, and a gyroscope.

In an embodiment, the motion circuitry comprises an accelerometer and a gyroscope. The motion circuitry may further comprise sensor fusion software for combining the accelerometer data and gyroscope data so as to provide physical quantities, such as acceleration data, velocity data, or limb trajectory data in a reference coordinate system having orientation defined by a predetermined gyroscope orientation.

In an embodiment, the motion circuitry comprises a gyroscope and a magnetometer. The motion circuitry may further comprise sensor fusion software to combine gyroscope data and magnetometer data so as to provide a reference coordinate system for the gyroscope based on the Earth magnetic field measured by the magnetometer. In general, the sensor fusion software described above may combine measurement data acquired from at least two motion sensors such that measurement data acquired from one motion sensor is used to establish the reference coordinate system for the measurement data acquired from at least one other motion sensor.

Still referring to FIG. 1, the heart activity measurement system may further comprise the external sensor device(s) 100, 104 used by the user 90. The external sensor device(s) 100, 104 may comprise sensors, such as a heart rate transmitter 100, a stride sensor, a positioning sensor, a cadence sensor and a power sensor, to mention a few. The heart rate transmitter 100 may comprise at least one electrical, optical and/or bioimpedance sensor to measure user's 90 heart activity. The electrical sensor(s) may be, for example, based on Electrocardiography (EKG) measurement. The positioning sensor may comprise a GPS, a magnetometer and/or a Bluetooth sensor. Thus, the positioning may be based on, for example, GPS location and/or Bluetooth location. The magnetometer may provide direction data based on magnetic fields on earth and/or inside structures.

The external sensor device(s) 100, 104 may be attached to the user 90. Thus, for example the heart rate transmitter 100 may be attached to the body tissue of the user 90. Further, the external sensor device(s) 100, 104 may detect the motion of the external sensor device(s) 100, 104 in relation to the body tissue of the user 90. This may be achieved by using motion sensor(s), and heart activity sensor(s) as described later in more detail.

The external sensor device(s) 100, 104 may comprise a head sensor, wherein the head sensor may be configured to measure heart activity of the user 90. The head sensor may be, for example, an ear sensor which may be placed within the user's 90 ear. The placement may be similar to placing earplug headphones. The head sensor may utilize optical measurement, bioimpedance measurement and/or EKG measurement for the heart rate measurement, for example. In an embodiment, the ear sensor is an in-ear sensor.

The external sensor device(s) 100, 104 may transmit the sensor data to the wrist device 102, to a portable electronic device 106 and/or to a server 114, residing in a network 110, of the heart activity measurement system. The portable electronic device 106 may be a mobile phone, a smart phone, a palm device, a tablet computer, phablet or a portable digital assistant, for example. The wrist device 102, the portable electronic device 106 and/or the server 114 may receive the sensor data. Similarly, the wrist device 102 may transmit the heart activity data, provided by the heart activity circuitry, and/or the motion sensor data, provided by the motion sensor, to the portable electronic device 106 and/or the server 114. The wrist device 102, the portable electronic device 106 and/or the server 114 may comprise at least one processor configured to process the received external sensor data, the heart activity data and/or the motion data into a set of metrics describing the user's 90 physical activity, such as heart rate of the user 90.

The external sensor device(s) 100, 104, the wrist device 102, the portable electronic device 106 and/or the server 114 may further comprise a communication circuitry, such as wireless communication circuitry, configured to enable sensor data transfer between the external sensor device(s) 100, 104, wrist device 102, portable electronic device 106 and/or the server 114.

Further, the wrist device 102, the external sensor device(s) 100, 104 and/or the portable electronic device 106 may comprise a memory, wherein the memory may be used by the devices to store the data from different sensor devices. The server 114 may use a database 112, such as a training database, to store the data. The database 112 may reside in the network 110.

In an embodiment, the external sensor device(s) 104 are comprised in the wrist device 102.

In an embodiment, the wrist device 102 further comprises at least one of the following sensors: a temperature sensor, a positioning sensor and a pressure sensor. The positioning sensor may utilize GPS and/or Bluetooth information for locating the user 90. Further, the positioning sensor may comprise a magnetometer and/or a compass.

The described heart activity measurement system may enable the user to track the heart activity from different devices. However, the heart rate transmitter 100 attached against a skin of the user 90 may be used to provide more accurate heart activity information compared to that of heart rate sensor(s) comprised in the wrist device 102, for example. Particularly, EKG-based heart rate measurement may be beneficial to apply in the heart rate transmitter 100. As described, the heart rate transmitter 100 may be used to measure heart activity-related data and transmit it to other devices of the physical activity measurement system that may be used to monitor the heart activity of the user 90. In order to do this, the EKG-based heart rate transmitter 100 may comprise an electrode belt coupled with an electronics unit. The electronics unit may be integral part of the electrode belt and/or detachable separate part of the heart rate transmitter, wherein the electronics unit may be detachably attached to the electrode belt.

As the electrode belt may be used to acquire heart activity information of the user 90, the electrode belt may need to be robust such that it may endure use in harsh environments. Further, it may be beneficial to make manufacturing of the electrode belt simple as it may bring savings in manufacturing costs. Thus, the structure of the electrode belt, and further the manufacturing of the electrode belt may be beneficial to enhance.

Figure 2A:
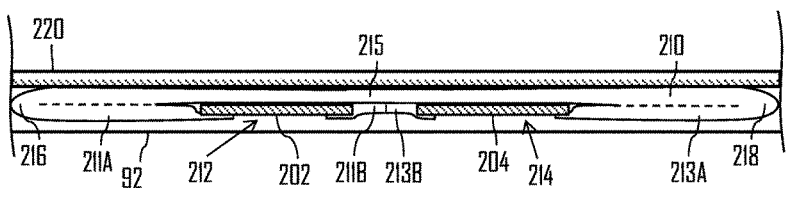
FIGS. 2A to 2D illustrate some embodiments of the invention.

FIG. 2A illustrates a cross-section of an electrode belt according to an embodiment of the invention. Referring to FIG. 2A, the electrode belt may comprise at least one electrode 202, 204 to measure biometric signals related to heart activity of the user 90. The at least one electrode 202, 204 may be made of and/or comprise electrically conductive Thermoplastic Polyurethane (TBU), for example. It may be possible to use other material(s) which are at least partially electrically conductive. For example, the at least one electrode 202, 204 may comprise material that has good gripping abilities, such as silicone. This may help the at least one electrode to be in good contact with the skin 92 of the user 90.

The at least one electrode may measure voltage variations on the skin of the user, wherein the variations are due to the activity of the heart muscle. As a result, an EKG signal may be generated. From the EKG signal, a variety of information may be derived. These include heart rate or heart rate variation, for example.

The electrode belt may further comprise a non-conductive strip 210 having at least one opening 212, 214, wherein the non-conductive strip 210 may comprise at least one fold 216, 218 such that at least two portions of the non-conductive strip 210 are folded against each other, and wherein the at least one electrode 202, 204 is positioned between the folded at least two portions of the non-conductive strip 210 so that the at least one electrode 202, 204 is enabled to be in physical contact with a skin 92 of the user 90 through the at least one opening 212, 214. As shown in FIG. 2A, the non-conductive strip 210 may extend at least partially over the at least one electrode 202, 204.

As shown in FIG. 2A, the at least two portions may comprise, for example, first portion 215, a second portion 211A, 211B, and a third portion 213A, 213B. The at least one electrode 202, 204 may be situated between the first portion 215, the second portion 211A, 211B, and the third portion 213A, 213B, for example. The second portion 211A, 211B may comprise the opening 212, for example. Similarly, the third portion 213A, 213B may comprise the opening 214, for example. The second portion 211A, 211B and the third portion 213A, 213B may be against the first portion 215 around the at least one opening 212, 214 even though, in FIG. 2A, there seems to be gaps on the areas of the at least one electrode 202, 204.

Direction of the at least one fold 216, 218 may be diverging compared to a longitudinal axis of the non-conductive strip 210. For example, looking at the example of FIG. 2A, the direction of the at least one fold 216, 218 may be seen to be substantially perpendicular to the longitudinal axis of the non-conductive strip 210. Thus, the direction of the at least one fold 216, 218, in FIG. 2A for example, may be understood to be substantially perpendicular to the longitudinal axis of the non-conductive strip 210. Therefore, the at least one fold 216, 218 may be diverging compared to the longitudinal axis of the non-conductive strip 210. This may mean that the at least one fold 216, 218 may not be parallel to the longitudinal axis of the non-conductive strip 210. The described folding may be effectively made on a strip-like material, such as the non-conductive strip 210, and may be easier and/or more accurate to manufacture compared to a longitudinal folding, as the folding needs to be performed on a shorter length on the non-conductive strip 210 compared to the longitudinal folding.

Figure 2B:
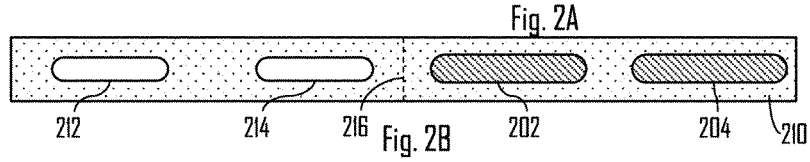
Figure 2C:
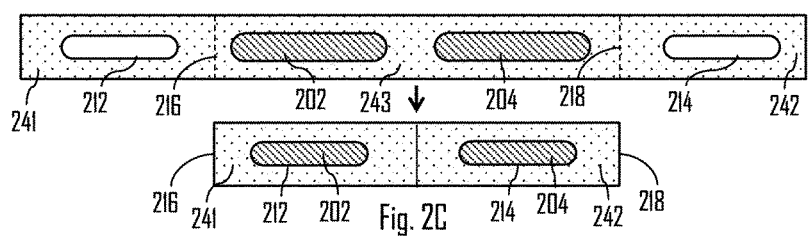

To even more precisely describe the direction of the at least one fold 216, 218, let us look at the example of FIG. 2C. The direction of the at least one fold 216, 218 may mean the direction shown with dash lines 216, 218. As shown in FIG. 2C, said direction of the at least one fold 216, 218 may be substantially perpendicular to the direction of the longitudinal axis of the non-conductive strip 210, for example. As described above, the direction of the at least one fold 216, 218 may be diverging compared to the longitudinal axis of the non-conductive strip 210. Therefore, it may be possible that the at least one fold 216, 218 is not substantially perpendicular to the direction of the longitudinal axis, but still is diverging from the direction of the longitudinal axis of the non-conductive strip 210. The at least one fold 216, 218 may be, for example, skew compared to the example shown in relation to FIG. 2C. In such case, the non-conductive strip 210 may need to be formed so that, for example, the at least one opening 212, 214 is situated so that the at least one electrode 202, 204 may be enabled to be in contact with the skin 92.

In an embodiment, the at least one fold 216, 218 is substantially perpendicular to the longitudinal axis of the non-conductive strip 210.

In an embodiment, the at least one fold 216, 218 is substantially diverging compared to the longitudinal axis of the non-conductive strip 210. This may mean that the length, measured along the longitudinal axis, of the non-conductive strip 210 may become shorter after the at least one fold 216, 218 is performed.

In an embodiment, the at least two portions of the non-conductive strip 210 are folded against each other such that they are at least partially overlapping, and wherein the folding is performed so that the folding direction is substantially diverging from the direction of the longitudinal axis of the non-conductive strip 210.

The folded at least two portions of the non-conductive strip 210 may be attached together so that the at least one electrode 202, 204 may be sealed within the non-conductive strip 210. Naturally, the at least one opening 212, 214 may enable the at least one electrode 202, 204 to be in physical contact with the skin 92 of the user 90, and thus the sealing may not fully enclose the at least one electrode 202, 204 within the non-conductive strip 210.

The non-conductive strip 210 may be a sheet of material that is used as a substrate for the at least one electrode 202, 204. In an embodiment, the non-conductive strip 210 comprises a non-conductive film. In another embodiment, the non-conductive strip 210 is a non-conductive base structure of the electrode belt. The non-conductive strip 210 may be at least partially elastic and/or flexible. This may further help the at least one electrode 202, 204 to be in contact with the skin 92 of the user 90.

The at least one fold 216, 218 may be achieved and/or performed in many ways. These may be discussed later in more detail. However, looking at the example of FIG. 2A, the non-conductive strip 210 may comprise two folds, wherein a first and a second portions of the non-conductive strip 210 are folded against a third portion of the non-conductive strip 210, thus partially encapsulating the at least one electrode 202, 204 between the portions of the non-conductive strip 210.

The at least one fold 216, 218 used to partially encapsulate and/or hold the at least one electrode 202, 204 may be beneficial as the at least one electrode 202, 204 may be thus electrically insulated from each other and/or from nearby element(s). Further, manufacturing of such structure may be easier as the non-conductive strip 210 may be of one integral entity, and thus the positioning of the at least one electrode 202, 204 to the non-conductive strip 210 may not require two or more non-integral layers. This may also make the electrode belt, and particularly, the electrode(s) more robust as the at least one fold 216, 218 may better protect the at least one electrode 202, 204 from, for example, moisture and/or humidity.

In an embodiment, the non-conductive strip 210 may be made of and/or comprise TBU that is not conductive. The non-conductive material may help the non-conductive strip 210 to electrically isolate the two or more electrodes 202, 204 from each other. Thus, the measurement may be enhanced.

In an embodiment, the non-conductive strip 210 is a non-conductive sheet strap forming an integral entity.

In an embodiment, the non-conductive strip 210 comprises a polyurethane coating, such as TBU coating.

In an embodiment, the non-conductive strip 210 may be referred to as a first substrate strip being substantially non-conductive.

Further, the electrode belt may comprise a flexible strip 220 to enable placement of the electrode belt against the skin 92 of the user 90, wherein the non-conductive strip 210 is coupled with the flexible strip 220 such that, when in use, the at least one electrode 202, 204 is in physical contact with the skin 92 of the user 90. The flexible strip 220 may be known also as a base layer or a supporting layer, for example. The flexible strip 220 may comprise woven or knitted textile with elastic components, such as rubber and/or thermoplastic. The flexible strip 220 may form a substrate for mounting the non-conductive strip 210.

In an embodiment, the flexible strip 220 is at least partially elastic.

In an embodiment, the flexible strip 220 is a flexible strap.

In an embodiment, the flexible strip 220 is a flexible substrate. The flexible substrate may be, for example, a flexible textile substrate.

In an embodiment, the non-conductive strip 210 may be referred to as a second substrate being substantially flexible.

In an embodiment, the flexible strip 220 is bendably flexible (e.g. flexible so that the flexible strip 220 may be bent, flexed or twisted without breaking). In an embodiment, the flexible strip 220 is stretchably flexible (e.g. flexible so that it may be stretched in longitudinal and/or transversal direction).

There may be multiple ways to couple the non-conductive strip 210 with the flexible strip 220. These may be discussed later in more detail. In the example of FIG. 2A, the non-conductive strip 210 may be attached to the flexible strip 220 using an adhesive and/or an adhesive film between the non-conductive strip 210 and the flexible strip 220.

The flexible structure of the electrode belt may enable the at least one electrode 202, 204 to be in contact with the skin 92 of the user 90. The electrode belt may, when in use, follow the curves of the skin 92, and thus the electrodes 202, 204 may be in contact with the skin 92. This may be enabled by one or more things: the flexible strip 220, the flexible non-conductive strip 210, the thinness of the non-conductive strip 210 and/or the flexible at least one skin electrode 202, 204. Further, the non-conductive strip 210 may be folded over the at least one electrode 202, 204 so that the at least one electrode 202, 204 extends, at least partially, through the at least one opening 212, 214. Thus, when the electrode belt is in use, the at least one electrode 202, 204 may be the first to contact the skin 92.

It needs to be noted that the portion(s) of the non-conductive strip 210 reaching over the at least one electrode 202, 204 in FIG. 2A may be much thinner in practice. Thus, the at least one electrode 202, 204 may be, in practice, substantially as close and/or closer to the skin 92 compared to any portion(s) of the non-conductive strip 210. Further, as the skin 92 of the user 90 may flex, and the electrode belt may flex, the at least one electrode 202, 204 may be in contact with the skin 92 of the user 90, although the non-conductive strip 210 would be closer to the skin 92 of the user 90. Firm attachment of the electrode belt may enhance the contact between the at least one electrode 202, 204 and the skin 92.

In an embodiment, the non-conductive strip 210 is thinner compared to the at least one electrode 202, 204. This may further enhance the connection between the at least one electrode 202, 204 and the skin 92.

In an embodiment, the at least one electrode 202, 204 is substantially convex or concave on the side that is placed against the skin 92. This may further enhance the connection between the at least one electrode 202, 204 and the skin 92, as the convex electrode may reach better through the opening, and the concave electrode may better follow the form of the skin 92 or body of the user 90.

It further needs to be noted that the non-conductive strip 210 and/or the flexible strip 220 may be manufactured by clipping wanted length strips from at least one coil of strip material. Thus, for example, the non-conductive strip 210 may be manufactured by clipping the non-conductive strip 210 from the coil of strip material. It may be an efficient way to produce the electrode belt from materials that are clipped from the at least one coil. Further, the at least one electrode 202, 204 may be also clipped from a coil of electrode strip. Thus, basically the electrode belt, as described in relation to FIG. 2A, may be manufactured using three coils of different strips, a first coil comprising electrode strip, a second coil comprising non-conductive strip and a third coil comprising a flexible strip, such as flexible and/or elastic textile.

FIG. 2B illustrates an embodiment of the invention. Referring to FIG. 2B, the non-conductive strip 210 may comprise one fold 216 such that two portions of the non-conductive strip 210 are folded against each other, wherein the at least one electrode 202, 204 is positioned between the folded two portions so that the at least one electrode 202, 204 is enabled to be in physical contact with the skin 92 of the user 90 through the at least one opening 212, 214. For example, one portion shown in FIG. 2B may be the portion of the non-conductive strip 210 that comprises the at least one opening 212, 214, and the other portion may be the portion that comprises the at least one electrode 202, 204. Dividing line between said portions may be the fold 216, for example. However, it may be possible to fold said portions so that ends of said portions are not placed against each other. Thus, one portion may be larger compared to another, for example.

The at least one electrode 202, 204 may comprise two or more electrodes 202, 204, and the non-conductive strip 210 may comprise two or more openings 212, 214 to enable the two or more electrodes 202, 204 to be in physical contact with the skin 92 of the user 90. As shown in FIG. 2B, the electrodes 202, 204 may be situated in one portion of the non-conductive strip 210, and the openings 212, 214 may be comprised in another portion of the non-conductive strip 210. The fold 216 may act so that the electrodes 202, 204 may be at least partially visible, and enabled to be in contact with the skin, through the openings 212, 214.

In an embodiment, one or more openings 212, 214 are used for two or more electrodes 202, 204. Thus, the electrode belt may comprise, for example, two electrodes 202, 204 that are in contact with the skin 92 through only one opening 212, 214.

FIG. 2C illustrates an embodiment of the invention. Referring to FIG. 2C, the non-conductive strip 210 may comprise two or more folds 216, 218, as was also shown in relation to FIG. 2A. The non-conductive strip 210 may comprise the two or more folds 216, 218 such that a first and a second portions 241, 242 of the non-conductive strip 210 are folded against a third portion 243 of the non-conductive strip 210, wherein the first portion 241 is situated at a first end of the non-conductive strip 210 and the second portion 242 is situated at a second end of the non-conductive strip 210, wherein the third portion 243 is situated between the first and the second portions 241, 242, and wherein at least a first electrode 202 of the two or more electrodes 202, 204 is positioned between the first and the third portions 241, 243 and a second electrode 204 of the two or more electrodes 202, 204 is positioned between the second and the third portions 241, 243. This may be shown in FIG. 2C.

As shown in FIG. 2C, the first portion 241 may be folded over the first electrode 202 so that a first opening 212 of the at least one opening 212, 214 is situated on top of and/or below the first electrode 202. Similarly, the second portion 242 may be folded over the second electrode 204 so that a second opening 214 of the at least one opening 212, 214 is situated on and/or below the second electrode 204. Thus, both electrodes 202, 204 may be enabled to be in contact with the skin 92 of the user 90.

As shown in FIGS. 2B and 2C, width of the at least one electrode 202, 204 may be smaller compared to the width of the non-conductive strip 210. The width of the at least one electrode 202, 204 may mean the shorter side of the at least one electrode 202, 204 in FIGS. 2B and 2C. This may help the at least one electrode 202, 204 to be sealed, partially, within the non-conductive strip 210 as the edges of the non-conductive strip 210 may be against each other when the two or more folds 216, 218 are performed. For example, as the first portion 241 is folded against the third portion 243, the first portion 241 may be against the third portion 243 around the first electrode 202. Thus, the connection between the first portion and the third portion may encircle the first electrode 202. Similarly, the second electrode may be encircled by the connection between the second portion 242 and the third portion 243.

Naturally, as shown in FIGS. 2B and 2C, the length of the at least one electrode 202, 204 may be shorter than length of half of the non-conductive strip 210. If more than one electrode 202, 204 is used, the combined length of the more than one electrode 202, 204 may be shorter than the length of half of the non-conductive strip 210.

Further, the at least one opening 212, 214 may be dimensioned so that width and length of the at least one opening 212, 214 is smaller than the width and length of the at least one electrode 202, 204. This way it may be ensured that the at least one electrode 202, 204 fully accommodates the at least one opening 212, 214.

In an embodiment, the at least one opening 212, 214 is dimensioned so that the width and the length of the at least one opening 212, 214 is substantially the same than the width and length of the at least one electrode 202, 204.

In an embodiment, the folded at least two portions of the non-conductive strip 210, shown in FIG. 2B, are attached together using an adhesive. Similarly, the first and the third portions 241, 243 and the second and the third portions 242, 243 may be attached together using an adhesive.

In an embodiment, an adhesive is used to attach the at least one electrode 202, 204 to the non-conductive strip 210. This may further increase the robustness of the electrode belt, as the at least one electrode 202, 204 may be more firmly attached to the electrode belt.

In an embodiment, the non-conductive strip 210 comprises at least one adhesive film. The at least one adhesive film may be used to attach the at least one electrode 202, 204 to the non-conductive strip 210, for example. Further, the at least one adhesive film may be used to attach the folded at least two portions of the non-conductive strip 210 against each other. It may also be possible to use the at least one adhesive film to attach the non-conductive strip 210 to the flexible strip 220.

In an embodiment, a side of the non-conductive strip 210, on which the at least one electrode 202, 204 is situated, comprises an adhesive film. Further, an opposite side may comprise an adhesive film to enable attachment of the non-conductive strip 210 to the flexible strip 220.

In an embodiment, the folded at least two portions of the non-conductive strip 210, shown in FIG. 2B, are attached together using a hot melt-process. This may comprise using a hot melt adhesive, such as hot glue. Similarly, other element of the electrode belt may be attached using the hot melt-process. Thus, for example the at least one electrode 202, 204 may be attached to the non-conductive strip 210 using the hot melt-process.

In an embodiment, with reference to FIG. 2C, the first opening 212 is comprised in the first portion 241 of the non-conductive strip 210 and the second opening 214 is comprised in the second portion 242 of the non-conductive strip 210. In another embodiment, the third portion 243 comprises the first and the second openings 212, 214.

In an embodiment, with reference to FIG. 2B, the non-conductive strip 210 comprises one fold 216 such that two portions of the non-conductive strip 210 are folded against each other, wherein the at least one electrode 202, 204 is positioned between the folded two portions so that the at least one electrode 202, 204 is enabled to be in physical contact with the skin 92 of the user through the at least one opening 212, 214.

In an embodiment, the at least one electrode 202, 204 is encapsulated between the at least two portions so that the at least one electrode 202, 204 is at least partially visible through the at least one opening 212, 214. This may be shown in FIG. 2C, for example. The encapsulation may mean that the at least one electrode 202, 204 is encircled from all sides, excluding area directly on the at least one opening 212, 214, by the non-conductive strip 210.

Figure 2D:
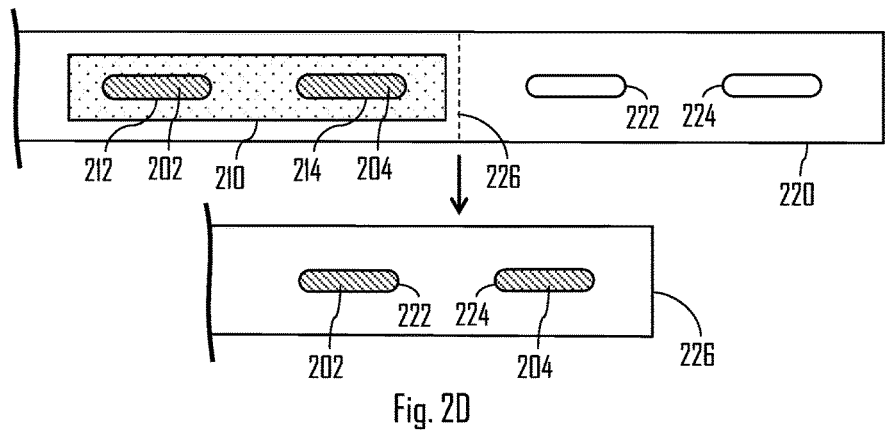

FIG. 2D illustrates an embodiment of the invention. The flexible strip 220 may be illustrated in two views, the upper view illustrating the flexible strip 220 before it has been folded, and the lower view illustrating the flexible strip 220 after it has been folded according to an embodiment. The lower view of the flexible strip 220 may show the side of the flexible strip 220 that is configured to be placed against the skin 92 of the user 90. Thus, the electrode(s) 202, 204 may be visible.

Referring to FIG. 2D, the flexible strip 220 comprises at least one fold 226 such that at least two portions of the flexible strip 220 are folded against each other, wherein the flexible strip 220 comprises at least one opening 222, 224, the non-conductive strip 210 being positioned between the folded at least two portions of the flexible strip 220 so that the at least one opening 212, 214 of the non-conductive strip 210 and the at least one opening 222, 224 of the flexible strip 220 are substantially aligned and against each other enabling the at least one electrode 202, 204 to be in contact with the skin 92 of the user 90. Situating the non-conducting strip 210 and the at least one electrode 202, 204 may give extra robustness for the electrode belt. For example, the flexible strip 220 may decrease an effect of external forces to the at least one electrode 202, 204. Further, the flexible strip 220 may decrease the amount of moisture getting to the non-conducting strip 210, thus decreasing the risk of short-circuiting, for example.

In an embodiment, the direction of the at least one fold 226 may be diverging compared to a longitudinal axis of the flexible strip 220. This may be understood similarly as the direction of at least one fold 216, 218 of the non-conductive strip 210.

Even though FIG. 2D illustrates the folding of the flexible strip using one fold to partially encapsulate the non-conductive strip 210, it may be equally possible to use two or more folds similarly as in FIG. 2C, for example.

In an embodiment, the at least one opening 222, 224 of the flexible strip is dimensioned so that the width and the length of the at least one opening 212, 214 is substantially the same and/or smaller than the width and length of the at least one opening 212, 214 of the non-conducting strip 210.

In an embodiment, the at least two portions of the flexible strip 220 are attached together using an adhesive. It may be also possible to use the hot melt-process for the attachment, such as hot glue.

In an embodiment, the non-conductive strip 210 is attached from its ends to the ends of the flexible strip 220. Together, the non-conductive strip 210 and the flexible strip 220 may reach, for example, around the body of the user 90. In such case, the flexible strip 220 may not necessarily reach to the area on which the measurement is performed. This approach may save material in the manufacturing process.

Figure 3A:
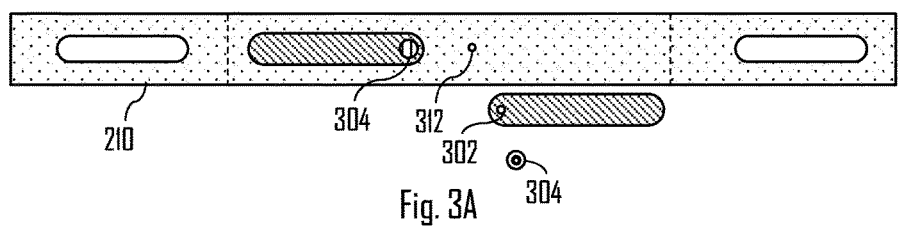
FIGS. 3A to 3B illustrate some embodiments of the invention.
Figure 3B:
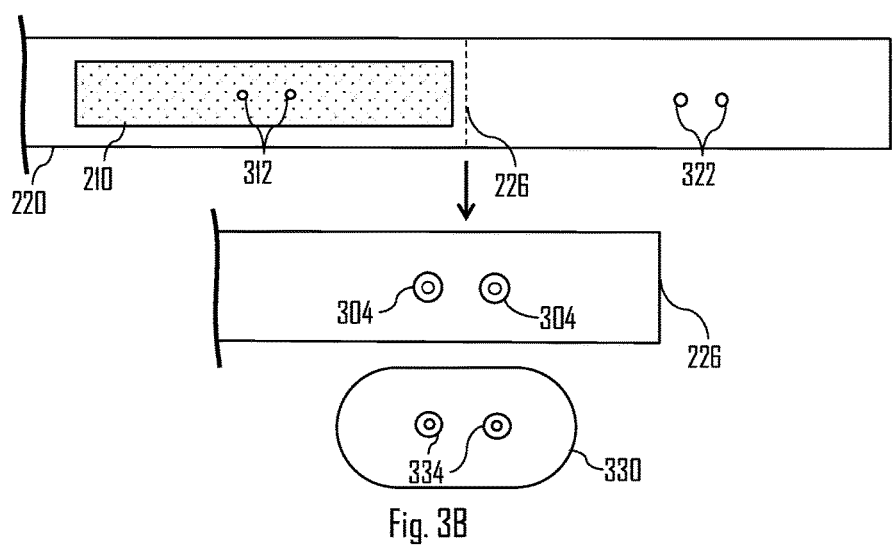

FIGS. 3A to 3B illustrate some embodiments of the invention. Referring to FIGS. 3A to 3B, the electrode belt may further comprise at least one coupling member 304 at least to enable electrical coupling of the at least one electrode 202, 204 with an electronics unit. As described earlier, the electrode belt, and more particularly, the electrode(s) may function together with the electronics unit 330 shown in FIG. 3B. The electronics unit 330 may be further discussed in relation to FIG. 6, but it may comprise, for example, a processing circuitry to process the biometric signals from the at least one electrode 202, 204, and a communication circuitry for transmitting the heart activity data to an external device, such as the wrist device 102. The wrist device 102 may be configured to receive the data and process the data into heart activity information of the user, for example. Further, other metrics, such as energy expenditure, may be derivable from the information by the wrist device 102.

In an embodiment, the at least one coupling member 304 is further adapted to enable attachment of the electronics unit 330 to the electrode belt.

FIG. 3B may show the non-conductive strip 210 positioned at one part of the flexible strip 220. As the fold 226 may be performed, the non-conductive strip 210 may be situated between the at least two portions of the flexible strip 220. The at least one electrode 202, 204 may not be visible as they may be visible on the opposite side of the non-conducting strip 210 shown in FIG. 3B. Thus, the at least one opening 212, 214 of the non-conductive strip 210 and the at least one opening 212, 214 of the flexible strip 220 may be located behind the conductive strip 210 in FIG. 3B. Thus, the side of the flexible strip 220, shown in FIG. 3B after the fold 226 is performed, may be the side that is facing outwards from the skin 92 of the user 90, when in use.

As shown in FIGS. 3A to 3B, the non-conductive strip 210 may comprise at least one through-hole 312 for the at least one coupling member 304. Similarly, the at least one electrode 202, 204 may comprise at least one hole and/or opening corresponding to the at least one through-hole 312 of the non-conductive strip 210.

As shown in FIG. 3B, the flexible strip 220 may comprise at least one through-hole 322 for the at least one coupling member 304. Referring to FIG. 3B, the non-conductive strip may be positioned to the flexible strip 220 so that the at least one through-hole 312 of the non-conductive strip 210 and the at least one through-hole 322 of the flexible strip 220 are substantially aligned and against each other.

In an embodiment, the at least one coupling member 304 reaches through the at least one through-hole 312 of the non-conductive strip 210 and/or the at least one through-hole 322 of the flexible strip 220. Therefore, if the at least one electrode 202, 204 is situated within the folded at least two parts of the non-conductive strip 210, and the non-conductive strip 210 is situated between the folded at least two parts of the flexible strip 220, the at least one coupling member 304 may reach all the way through the different parts of the electrode belt from the at least one electrode 202, 204 to the electronics unit 330.

Each of the at least one coupling member 304 may comprise, for example, a protrusion extending through the at least one electrode 202, 204 and the at least one through-hole 312 of the non-conductive strip 210. As shown, in FIG. 3A, the protrusion may be connected with a base that may be dimensioned to have a greater diameter compared to the diameter of the at least one through-hole 312 of the non-conductive strip 210. The base and/or protrusion may be in contact with the at least one electrode so that there may be an electrical connection between at least one coupling member 304 and the at least one electrode 202, 204.

The protrusion may further extend through the at least one through-hole 322 of the flexible strip 220, when the at least two parts of the flexible strip 220 have been folded against each other. The at least one coupling member 304 may further comprise a connection member coupled with the protrusion, locking the at least one coupling member 304 in its place together with the base of the at least one coupling member 304. The connection member may be, for example, a female part or socket of a snap fastener, as shown in FIG. 3B.

It needs to be further noted that the base of the at least one coupling member 304 may be situated so that it may not be visible through the at least one opening 212, 214. This may be beneficial as then the at least one coupling member 304 may not be in direct contact with the skin 92 of the user 90. It may be rather uncomfortable for the user 90 if the at least one coupling member 304 rubs against the skin 92 of the user 90.

In an embodiment, as shown in FIGS. 3A and 3B, the at least one coupling member 304 comprises at least a first part of a snap fastener and/or a similar component. Each of the at least one coupling member 304 may comprise the first part of the snap fastener.

In an embodiment, the electronics unit 330 comprises at least one connection member 334, wherein the at least one connection member 334 is adapted and dimensioned to enable detachable attachment of the electronics unit 330 to the electrode belt. The at least one connection member 334 may be a counterpart for the at least one coupling member 304. The at least one coupling member 304 and/or the at least one connection member 334 may enable electrical and/or physical connection between the electronics unit 330 and the electrode belt. For example, each of the at least one connection member 334 may comprise a second part of the snap fastener. Thus, the snap fastener may provide electrical connection between the electrode(s) 202, 204 and the electronics unit 330. Further, the snap fastener may mechanically connect the electronics unit 330 to the electrode belt.

In an embodiment, the electronics unit 330 is configured at least to transmit information related to heart activity received from the at least one electrode 202, 204. As described earlier, the electronics unit 330 may further process the information related to heart activity before transmitting it. In an embodiment, the electronics unit 330 stores the information related to heart activity and/or processed information to a memory of the electronics unit 330 and/or an external device, such as wrist device 102, or database 112.

In an embodiment, the electrode belt comprises the electronics unit 330, wherein the electronics unit 330 is configured at least to transmit information related to heart activity received from the at least one electrode 202, 204. The transmission may be wireless, for example.

In an embodiment, the at least one connection member 334 comprises the second part of a snap fastener, and wherein the first and second parts of the snap fastener are adapted and dimensioned to enable detachable attachment of the electronics unit 330 to the electrode belt, and wherein the snap fastener enables electronic coupling between the at least one electrode 202, 204 and the electronics unit 330. Each of the at least one connection member 334 may comprise the second part of the snap fastener.

There is also provided a method for manufacturing the electrode belt, as shown in FIG. 3C, the method comprising: providing at least one electrode 202, 204 to measure biometric signals related to heart activity of a user (step 352), providing a non-conductive strip 210 having at least one opening (step 354), applying the at least one electrode 202, 204 on the non-conductive strip 210 (step 356), folding at least two portions of the non-conductive strip 210 against each other, wherein the at least one electrode 202, 204 is positioned between the folded at least two portions of the non-conductive strip 210 so that the at least one electrode 202, 204 is enabled to be in physical contact with a skin of the user through the at least one opening 212, 214 (step 358), providing a flexible strip 220 to enable placement of the electrode belt against the skin of the user (step 360), and coupling the non-conductive strip 210 to the flexible strip 220 such that, when in use, the at least one electrode 202, 204 is in physical contact with the skin of the user (step 362). The described method may make the producing of the electrode belt easier, as the material, or at least some of the materials, used may be fed from one or more coils. This may reduce the needed work steps, for example.

In an embodiment, the folding, in step 358, is performed in a direction that is divergent compared to the longitudinal axis of the non-conductive strip 210. Naturally, if more than one folding is performed, the folds may be all divergent compared to the longitudinal axis of the non-conductive strip 210. Further, the different folds may not necessarily be in the same direction, and thus the direction of different folds may be the same, and/or different.

Figures 4A, 4B, 4C:
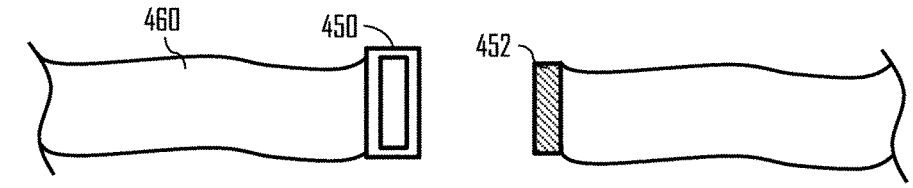

FIGS. 4A to 4G illustrate some embodiments of the invention. Referring to FIG. 4A, a heart rate transmitter structure 400 may be shown. The heart rate transmitter structure 400 may comprise an electrode belt 410, a holder unit 420 and an electronics unit 430. The electrode belt 410 may be and/or comprise the electrode belt described in relation to FIGS. 2A to 3B, for example. Similarly, the electronics unit 430 may be and/or comprise the electronics unit 330 described earlier. The holder unit 420 may comprise at least one coupling member 422 to enable electrical and/or mechanical connection between the electrode belt 410 and the electronics unit 430. The electronics unit 430 unit may comprise counterparts 432 for the at least one coupling member 422.

In an embodiment, the electrode belt 410 comprises at least one coupling member 422. In a scenario where the holder unit 420 may be used, the electrode belt 410 may together with the holder unit 420 comprise the at least one coupling member 422.

The holder unit 420 may be attached to the electrode belt 410. For example, adhesive and/or mechanical attachment, such as screw(s) may be used. The holder unit 420 may comprise a cavity 424 for the electronics unit 430 to be fitted in. This may be shown in more detail with reference to FIG. 4B.

In an embodiment, the holder unit 420 comprises two or more coupling members 422 and the electronics unit 430 comprises corresponding amount the counterparts 432 for the at least one coupling member 422.

Referring to FIG. 4B, the holder unit 420 may be elastic and/or flexible. The holder unit 420 may be made of and/or comprise TBU. The holder unit 420 may be adapted and dimensioned to receive the electronics unit 430 as shown in FIG. 4B, within the cavity 424. The holder unit 420 may produce force to the electronics unit 430 so that the counterparts 432 are pushed, by the produced force, substantially towards the at least one coupling member 422. Said force may be produced by snug fitting of the electronics unit 430 into the holder unit 420. For example, as the holder unit 420 may be elastic, the electronics unit 430 may be fitted on its place by twisting at least one side of the holder unit 420. As the twisting ends, the inner dimensions (e.g. inner sides) of the holder unit 420 may be smaller compared to the outer dimensions of the electronics unit 430. Therefore, the holder unit 420 may be at least partially stretched by the electronics unit 430 in the cavity 424, and the stretching may cause a counterforce that pushes the electronics unit 430 towards the at least one coupling member 422 and/or the skin 92 of the user 90. Thus, the force towards the at least one coupling member 422 and/or towards skin 92 of the user 90 may be produced.

In an embodiment, the holder unit 420 is adapted at least to enable attachment of the electronics unit to the electrode belt, wherein the holder unit 420 comprises the cavity 424, and wherein the holder unit 420 is adapted and dimensioned to receive the electronics unit at least partially within the cavity 424. This may mean that the electronics unit, such as the electronics unit 330 or the electronics unit 430, may be at least partially within the cavity 424. The user 90 may then more easily use the electronics unit if at least some parts of it are outside and/or visible through the cavity 424.

In an embodiment, the cavity 424 is dimensioned so that the electronics unit is substantially and/or totally within the cavity 424. Thus, the electronics unit, when fitted to the cavity 424, may be even better protected from external forces and/or humidity, for example.

Besides producing force towards the skin 92 of the user 90, the snug fitting of the electronics unit 430 into the holder unit 420 may enhance the robustness of the heart rate transmitter 400. For example, the holder unit 420 may provide protection against external forces. Further, the snug fitting may reduce and/or prevent moisture, such as water or sweat, from getting to inner parts of the electronics unit 430 or the counterpart(s) 432, for example.

As shown in FIG. 4B, the at least one coupling member 422 may comprise an opening in the electrode belt 410 and/or in the holder unit 420 as shown in FIG. 4B. In such case, the counterpart(s) 432 of the electronics unit 430 may be protrusion(s) 432 that extend to the opening(s) 422. The opening(s) 422 may reach to at least one electrode, such as the at least one electrode 202, 204, of the electrode belt 410, for example. Thus, the protrusion(s) 432 may be in electrical contact with the at least one electrode 202, 204. Naturally, the protrusion(s) 432 may be made of and/or comprise electrically conductive material.

In an embodiment, the protrusion(s) 432 and/or the opening(s) 422 comprise elastic material and/or are at least partially suspension. For example, the protrusion 432 may comprise a spring suspension or similar. This may further enable the electronics unit 430 to be in good contact with the electrode belt 410.

In an embodiment, the holder unit 420 is at least adapted to enable attachment of the electronics unit 430 to the electrode belt 410. Similar holder unit 420 may be used with the electrode belt of FIGS. 2A to 3B.

In an embodiment, the holder unit 420 comprises the at least one coupling member 422. Further, the holder unit 420 may comprise the at least one coupling member 304 shown in FIG. 3B, for example. Thus, the holder unit 420 may be individually used to physically attach the electronics unit to an electrode belt and/or the holder unit 420 may be used together with some other attachment member(s) to attach the electronics unit to said electrode belt. Thus, for example, magnetic locking, described in relation to FIG. 4D, may be used together with the holder unit 420, and/or snap fasteners may be used together with the holder unit 420. Even further, the holder unit 420 may be electrically isolated from the at least one coupling member 422 and/or the at least one coupling member 304. This may be caused by electrically non-conductive material used in the holder unit 420, for example.

In an embodiment, an electrode belt, such as the electrode belt 410 or the electrode belt described in relation to FIGS. 2A to 3B, comprises the electronics unit 430, wherein the electronics unit 430 is configured at least to transmit information related to heart activity received from the at least one electrode 202, 204. The transmission may be wireless transmission, for example.

In an embodiment, the electronics unit 430 is detachably attachable to an electrode belt, such as the electrode belt 410 or the electrode belt described in relation to FIGS. 2A to 3B, using the at least one coupling member, such as the at least one coupling member 422 or the at least one coupling member 304, and/or the holder unit 420. In other words, at least one of the at least one coupling member, the holder unit 420 may enable detachable attachment of the electronics unit 430 to the electrode belt.

There is provided an attachment mechanism according to an embodiment of the invention in FIG. 4C. Referring to FIG. 4C, at least one fastening member 450, 452 enabling detachable attachment of a strap 460 against the skin 92 of the user 90 may be shown. The strap 460 may, for example, the flexible strip 220. Thus, the at least one fastening mechanism 450, 452 may be used to detachably attach the electrode belt, shown in FIGS. 2A to 3B, and/or the electrode belt 410, for example.

The at least one fastening member 450, 452 may comprise, for example, two buckles 450, 452, one at one end of the strap 460 and other a second end of the strap 460, wherein the two buckles 450, 452 are adapted and dimensioned to attach to each other in detachable manner. Therefore, the user 90 may attach and/or release the strap 460 around his/her body, for example.

Referring to FIGS. 4D to 4G, a magnetic attachment mechanism may be shown. The attaching of the electronics unit 430 to the electronic belt 410 may comprise using magnetic material(s). Therefore, the at least one coupling member 422, comprised in the electrode belt 410 and/or the holder unit 420, may comprise magnetic material(s) and/or material(s) being magnetic when in a substantial magnetic field. This basically means that the material may be magnetic itself, such as neodymium magnet, or the material may be, for example, ferromagnetic, and thus responsive to magnets. Similarly, the counterpart(s) 432 may comprise magnetic material(s) so that the connection between the electronics unit 430 and the electrode belt 410 may be at least partially magnetic. For example, the at least one coupling member 422 may comprise iron and the counterpart(s) 432 may comprise neodymium magnet(s), or vice versa. Further, embodiments described in relation to magnetic attachment may be also used with the at least one coupling member 304 and/or the at least one connection member 334.

In an embodiment, the at least one coupling member 422 comprises at least one hollow and/or opening, wherein an inner surface of the at least one hollow and/or opening comprises at least one of a magnetic material, a material being magnetic when in a substantial magnetic field. The electronics unit 430 may comprise protrusion(s) reaching to the at least one hollow and/or opening, wherein the electronics unit 430 may be magnetically coupled with the at least one coupling member 422.

Using magnetic material in the attachment may cause magnetic field(s). The magnetic field(s) may in some cases cause interference to, for example, compass 492 or some other sensor(s) utilizing magnetic fields. As shown in FIG. 4E, the magnetic field between two magnets may reach rather far, and thus the compass 492 may be substantially interfered when in close proximity of the two magnets. As the distance increases to B, the interference may decrease substantially, and thus the compass 492 may work properly.

Hence, it may be beneficial, as shown in relation to FIG. 4F, to use a plurality of magnets in the attachment mechanism, wherein a first set of magnets may be placed adjacent to a second set of magnets so that opposite poles of the first set and the second set may be substantially opposite to each other. This may decrease the area of the magnetic fields generated by the magnets, and further may increase intensity of the magnetic fields. Thus, for example, if the first set comprises a first magnet 494 and the second set comprises a second magnet 496, the magnets 494, 496 may be placed adjacent to each other as shown in FIG. 4F. Further, the north pole of the first magnet 494 may be facing the south pole of the second magnet 496. Similarly, the south pole of the first magnet 494 may be facing the north pole of the second magnet 496. Using this approach may decrease the distance B of FIG. 4E to distance A, and thus the compass 492 may work more accurately closer to the magnetic attachment. This may cause a benefit for the user 90, as he/she may then be more confident on the compass 492 reading on the wrist device 102, for example. Further, as the distance A may be now shorter, when the wrist device 102 is lifted closer to the magnetic attachment on the heart rate transmitter and/or similar, the compass 492 reading may still be accurate. The first and second set of magnets may each comprise one to many magnets.

It may be also possible to use only one magnet to achieve the benefits described in relation to FIG. 4F, as shown in FIG. 4G. The magnet used in the attachment mechanism may be substantially U-shaped magnet. Thus, the opposite poles may be naturally opposite to each other. This may also decrease the distance B to distance C, thus decreasing the distance of substantial interference to the compass 492.

In an embodiment, the at least one coupling member 422 comprises the U-shaped magnet and/or the first set of magnets and the second set of magnets. In such case the counterpart(s) 432 may comprise, for example, ferromagnetic material and/or magnet(s).

In an embodiment, the counterpart(s) 432 comprises the U-shaped magnet and/or the first set of magnets and the second set of magnets. In such case the at least one coupling member 422 may comprise, for example, ferromagnetic material and/or magnet(s).

In an embodiment, the at least one coupling member 422 comprises the first set of magnets and the counterpart(s) 432 comprises the second set of magnets. Thus, opposite poles of the magnets may be used to connect the electronics unit 430 to the electrode belt 410.

In an embodiment, the at least one coupling member 422 and the counterpart(s) 432 comprise each the U-shaped magnet. In such case the U-shaped magnets may be placed to face each other so that the opposite poles are against each other.

In an embodiment, the counterpart(s) 432 comprise and/or are the at least one connection member 334. Similarly, the at least one coupling member 422 may comprise and/or be the at least one coupling member 304.

Figure 5A:
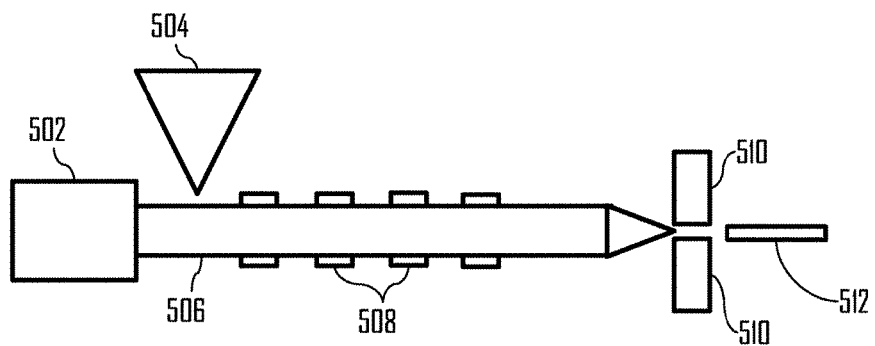
FIGS. 5A to 5F illustrate some embodiments of the invention.

FIGS. 5A to 5 F illustrate some embodiments of the invention. Referring to FIG. 5A, a manufacturing line may be shown. The manufacturing line may comprise a motor 502 to move material, a material provider 504 to portion out material to the manufacturing process, a manufacturing line 506 (e.g. screw) to move material according to the moving force induced by the motor 502, heater(s) 508 to heat the material to wanted temperature and/or a nozzle 510 to form the material into wanted thickness and/or to wanted width and height. The manufacturing process may produce a band-like material 512 that may be used in electrode belts, such as the electrode belt of FIGS. 2A to 3B and/or the electrode belt 410, for example. However, other types of electrode belts may be formed from the band-like material 512. The material which is used to manufacture the band-like material 512 may be, for example, conductive TBU and/or TBU.

In an embodiment, width of the band-like material 512 is greater than the thickness of the band-like material 512.

Figure 5B:
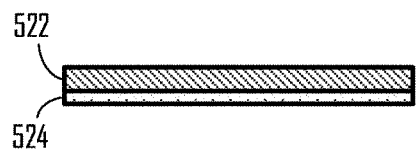

Referring to FIG. 5B, a material band comprising two layers 522, 524 may be shown. The first layer 522 may comprise conductive TBU, such as ester-based conductive plastic. The ester-based conductive plastic may have an ability to shrink over time, and thus may keep its conductive properties. This may happen as carbon-particles within may come closer to each other as the shrinking takes place. The second layer 524 may comprise adhesive, such as gradulate adhesive glue, which may be used to attach the material band into a substrate, such as the flexible strip 220 or similar, for example. Thus, the material band may act as at least one electrode, as the first layer 522 may be conductive. This material may be used to create the at least one electrode 202, 204, for example.

Figure 5C:
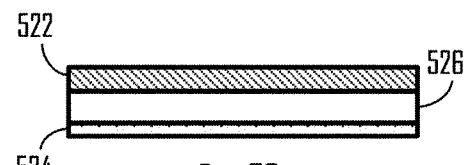

Referring to FIG. 5C, a material band comprising three layers may be shown. Now, compared to FIG. 5B, a third layer 526 may be positioned between the first and the second layers 522, 524. The third layer 526 may comprise TBU, for example, and may be non-conductive. This may enable the first layer 522 to be electrically insulated from the substrate to which it is attached to. This material may be used to create a combination of the at least one electrode 202, 204 and the non-conductive strip 210, for example. Therefore, it may be unnecessary to use adhesive to attach the at least one electrode 202, 204 to the non-conductive strip 210. This may make the manufacturing easier.

Figure 5D:
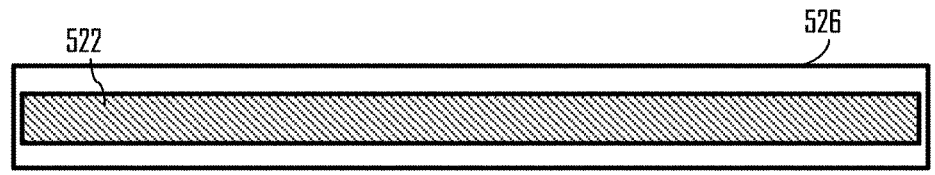
Figure 5E:
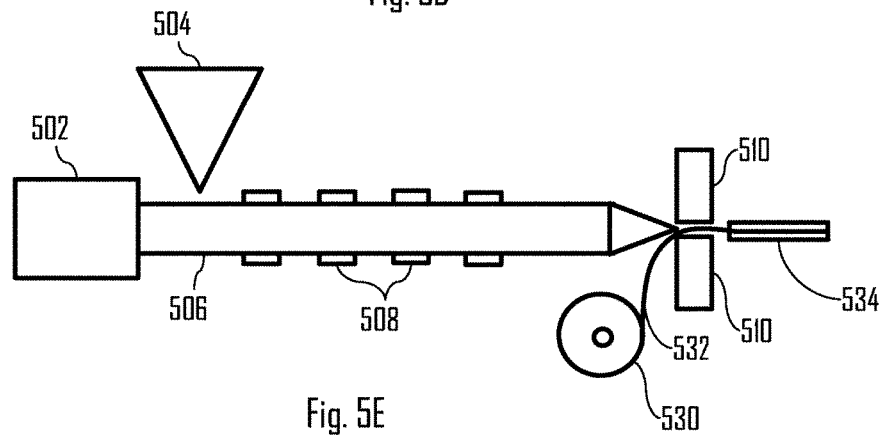

Referring to FIG. 5D, the first layer 522 on top of the third layer 526 may be shown from bird-eye perspective. The first layer 522 may be formed so that it may be narrower compared to the third layer 526. Further, if the material band of FIG. 5C is cut into pieces, cutting may be done so that the first layer 522 is at least slightly shorter compared to the third layer 526, as shown in FIG. 5D. Therefore, the first layer 522 may be electrically insulated from the substrate, as it may only be attached and/or touching the third layer 526. Naturally, the second layer 524 may cover the bottom area of the third layer 526, and thus the third layer 526 may be effectively attached to the wanted substrate.

In an embodiment, the material band (s) of FIGS. 5B and 5C are clipped into 15 to 20 centimeter long pieces.

In an embodiment, the first and the third layer 522, 526 are attached together using heating. Thus, the layers 522, 526 may be vulcanized together. For example, the layers 522, 526 may arrive from two similar processes (e.g. process of FIG. 5A) to a process step where the layers 522, 526 are jointed together as they are preheated in said processes. The jointing may mean that the layers 522, 526, at least partly, melt into each other. In another embodiment, an adhesive is used to attach the layer 522, 526 together.

In an embodiment, the at least one of the materials described in relation to FIGS. 5B to 5C are used in making the electrode belt 410. For example, two pieces of material described in relation to FIG. 5C may be attached to the flexible strip 210. Further, the electronics unit 330 may be coupled with the electrodes of said material.

Referring to FIG. 5 E, the process of FIG. 5A may further comprise a thread-holder 530 and/or a thread 532 fed into the process. The process may be referred to as an extrusion process, for example. The thread 532 may comprise, for example nylon, wool and/or polyester. The thread 532 may be referred to as a yarn. Further, the thread 532 may be any kind of thread which may be used for making clothes.

Figure 5F:
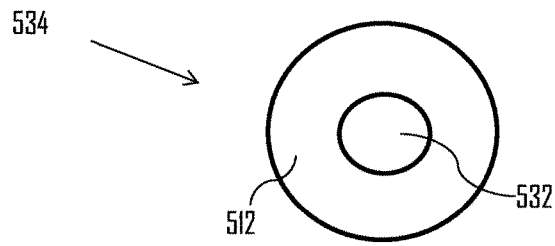

As the thread 532 may be fed through the nozzle 510, the material 534 may comprise the material 512 and the thread 532. The material 534 may be shaped as thread or a yarn, for example, wherein the shaping may be caused by the form of the nozzle 510. For example, the nozzle may be substantially rounded. The material 512, such as conductive TBU may surround the thread 532, as shown in FIG. 5F, and thus the material 534 may be used as a conductive thread and/or conductive yarn for making clothes, for example.

The material 534 may be applicable to some other knitting, sewing and/or needlework too, where electrical conductivity is required from the material 534. For example, it may be possible to use the material 534 to sew electrode(s) directly to clothes used during an exercise. Thus, separate electrode belt may not be required. Further, it may be possible to sew the electrode(s) 202, 204 to the electrode belt of FIGS. 2A to 3B, using the material 534. Thus, the electrode(s) 202, 204 may be sewn directly to a textile substrate providing a pleasant user experience, as a textile belt may be comfortable to use.

Figure 6:
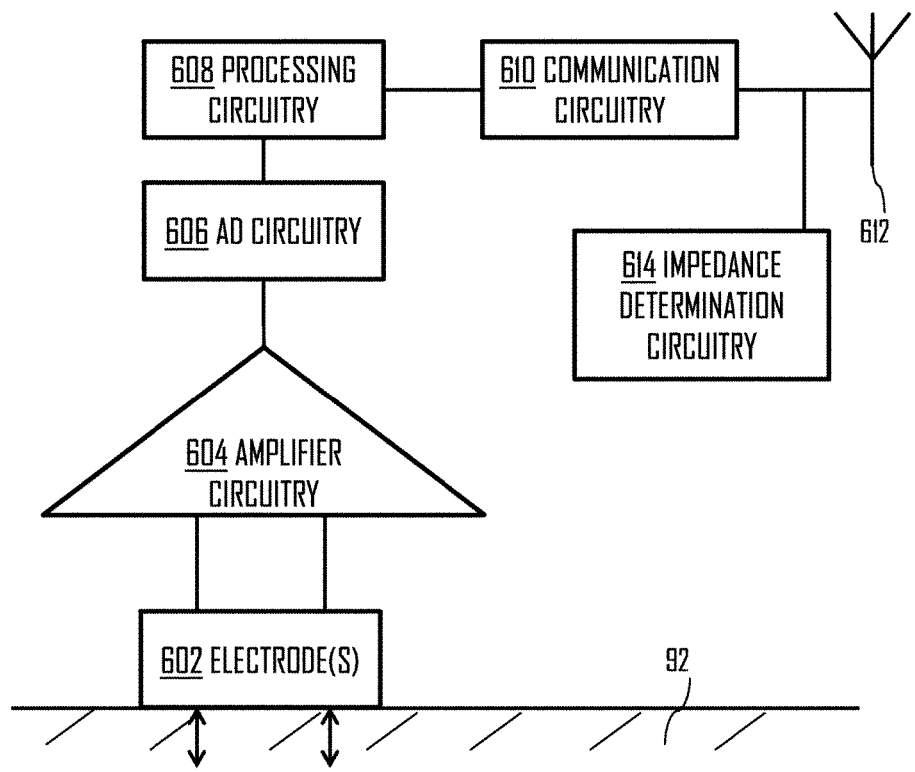
FIG. 6 illustrates an embodiment of the invention.

FIG. 6 illustrates an embodiment of the invention. Referring to FIG. 6, an electrode belt, such as the electrode belt 410 or the electrode belt of FIGS. 2A to 3B, may comprise electrode(s) 602. The electrode(s) 602 may be in contact with the skin 92, and thus provide biometric signals that may be used to determine heart activity of the user 90. The electrode(s) 602, as described earlier, may be connected to the electronics unit 330 and/or the electronics unit 430. In sake of simplicity, let us now look closer on the electronics unit 330 as the electronics unit 430 may be similar to electronics unit 430.

The electronics unit 330 may comprise an amplifier circuitry 604 (i.e. differential amplifier) may be used to amplify and/or separate the biometric signals acquired from the electrode(s) 602. For example, one biometric signal may be used to reduce and/or remove interference from another biometric signal using the differential amplifier.

The electronics unit 330 may further comprise an analog-to-digital converter circuitry (AD) 606. Thus, the biometric signals, or the amplified biometric signals, may be converted into digital form before processed in a processing circuitry 608. The processing circuitry 608 may be comprised in the electronics unit 330, and may comprise at least one processor and at least one memory including computer program code, wherein the at least one memory and the computer program code are configured, with the at least one processor, to cause the electronics unit to perform operations described later in relation to FIG. 7, for example.

Further, the electronics unit 330 may comprise a communication circuitry 610 configured to transmit and/or receive information. The communication circuitry 610 may support communication according to, for example, Bluetooth, Bluetooth Low Energy (BLE), Near-Field-Communication (NFC) and/or WiFi technologies, to name a few examples. The electronics unit 330 may further comprise sensor(s), such as GPS sensor and/or the motion circuitry, for example.

The electronics unit 330 may comprise at least one antenna 612 to enable the communication circuitry and/or the GPS sensor to transmit and/or receive information, such as GPS coordinates and/or Bluetooth beacon signals.

In an embodiment, the electronics unit 330 comprises one or more electrodes to measure heart activity of the user 90. For example, the electronics unit 330 may be placed into the holder unit 420, wherein the opening(s) 422 may be used to get the one or more electrodes directly in contact with the skin 92 of the user 90. Thus, the electrodes may be directly placed to the electronics unit 330 and the electrode belt would then operate as a holder for the electronics unit 330.

In an embodiment, the wrist device 102 and/or the portable electronic device 106 comprise at least some of the circuitries shown in FIG. 6. Further, the wrist device 102 may comprise at least one electrode for the heart rate measurement.

Figure 7:
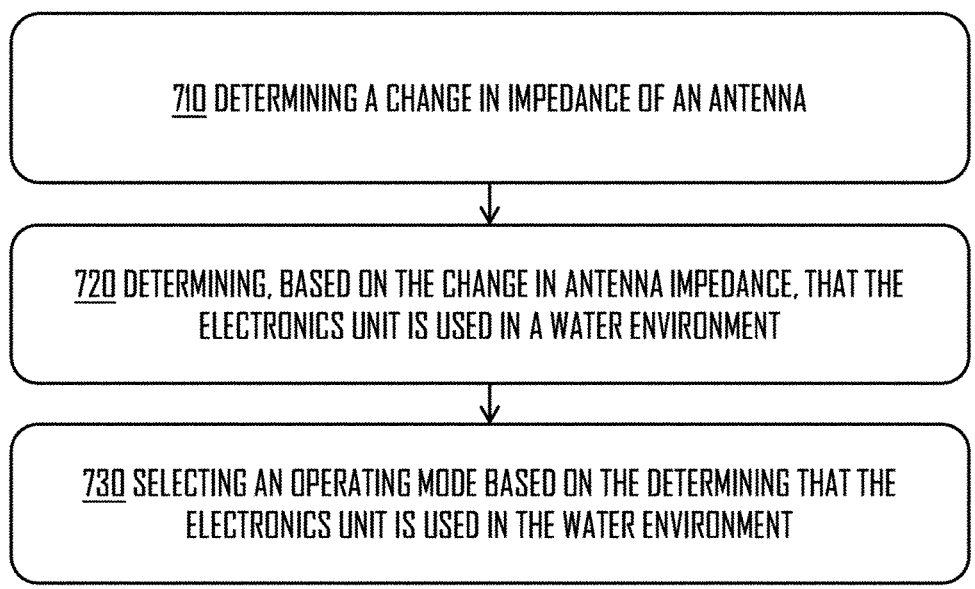
FIG. 7 illustrates a block diagram according to an embodiment of the invention.

FIG. 7 illustrates a block diagram according to an embodiment of the invention. Referring to FIG. 7, a training device, such as the electronics unit(s) 330, 340, the electrode belt(s) in combination with the electronics unit(s) 330, 340 (e.g. the heart rate transmitter), wrist device 102, portable device 106 or external sensor device(s) 100, 104 to name a few examples, may determine a change in impedance of an antenna (step 710). The training device may determine the change in its own antenna(s) and/or on an external device antenna. For example, the wrist device 102 may determine the impedance change in its own antenna and/or it may receive information from the electronics unit 330 from which the impedance change in the electronics unit 330 may be determined. As shown in FIG. 6, the electronics unit 330 and/or the electronics unit 430 may comprise an impedance determination circuitry 614 that may be configured to determine impedance of the antenna 612, for example.

Different methods may be used for the determination by the impedance determination circuitry 612. One example may be the use of RF-Bridge (based on Wheatstone Bridge), wherein at least one of the branches of the RF-Bridge comprises the antenna for transmission and/or receiving. In normal operating environment (air and next to skin), the antenna impedance may be, for example, 50 ohms. When in water, the impedance may increase rather drastically, and thus the branches of RF-Bridge may have different impedances compared to each other. This change may be detected using a diode detector and measuring the diode detector voltage with an analog-to-digital-converter circuitry and/or some threshold circuitry, for example. These detector(s) may be comprised in the impedance determination circuitry 614.

In step 720, the training device may determine, based on the change in impedance of the antenna, that the training device is used in a water environment. The water environment may mean that the training device is at least partly in the water for a predetermined amount of time within a measuring period. For example, the training device may be determined to be in the water environment when the training device is in the water when the user 90 is swimming, although the training device may be in the water for only a certain time, as the hand of the user 90 may rise above the water (and the training device may be attached to the hand of the user 90).

In an embodiment, the step 710 may be replaced and/or supplemented by using a barometer by the training device. The barometer may detect atmospheric pressure changes when the training device is underwater and/or going underwater. The barometer may work in scenarios, wherein the user 90 is diving underwater as then the change in pressure may be rather fast, and may be of same magnitude as pressure change in a freefall. To differentiate from the freefall scenario, the motion and/or position sensor(s) may be used by the training device.

Further, in another embodiment, the underwater condition may be determined, at least partly, using conductivity measurement on conductive outer part(s), such as metallic buttons and/or connection members, of the training device. As the training device is underwater, the conductive outer part(s) may be connected to a zero potential, for example. The water may between the conductive outer part(s) and the zero potential may cause and impedance which may then cause leakage of electricity. By using a separate conductivity determination circuitry, the training device may determine said leakage, and thus determine that the training device is underwater. The conductivity determination circuitry may comprise, for example, an analog-to-digital-converter circuitry to determine the leakage by taking samples from another branch of the conductivity determination circuitry after and before the training device goes underwater. As the electricity may, when in water, leak through the outer part(s), the samples may be different (mainly voltage may drop due to leakage), and thus the underwater condition may be detected. Further, at least one capacitor may be used with the conductivity determination circuitry.

In step 730, the training device may select an operating mode based on the determining that the training device is used in the water environment. The operating mode may mean a number of different things. For example, when in water the training device may stop transmitting and/or actively receiving (i.e. scanning mode of BLE). In another embodiment, the training device may start to transmit with a shorter interval. The stopping of transmission and/or transmitting with a shorter interval may refer to, for example, Bluetooth circuitry of the training device. It may be, however, possible that the training device continues to transmit and/or receive using another communication technology, such as 5 GHz and/or ultrasound, to enhance the penetration of the water. These communication technologies may be supported by the communication circuitry 610 and/or the antenna 612, for example.

Further, when in water, the training device may change parameters of the GPS sensor and/or antenna, such as the antenna 612. For example, the training device may stop receiving GPS signals as they may more easily be corrupted and/or faulty. Instead, the training device may use the motion circuitry) to determine, for example, travelled distance. In another example, the training device may increase sampling interval of the GPS signal. This may increase the change of receiving an uncorrupted GPS signal. For example, when the user 90 is swimming, user's 90 hand(s) may be in the air for a certain amount of time. During this time the training device, such as the wrist device 102, may be also in the air. Thus, when the sampling interval is such that the GPS signals is received during the time that the wrist device 102 is in the air, the measurement may be enhanced.

Even further, in other scenarios also Bluetooth, or similar, sampling interval and/or transmission may be increased. For example, if the user 90 is swimming and his mobile phone is at a side of pool, the wrist device 102 may transmit data successfully to the mobile phone during the time that the wrist device 102 is in the air.

In an embodiment, the training device stops recognizing gestures when the training device is determined to be in water. This may be beneficial as gestures may be used to control at least some functions of the training device. In water however at least some of these gestures may be discarded, and thus the user 90 may more freely perform the task at hand, such as swimming. For example, a gesture for answering a phone call by the wrist device 102 may be discarded. In an embodiment, the user 90 may select which gesture(s) should be discarded when the training device is in the water environment.

In an embodiment, the training device comprises at least one sensor and at least one antenna capable of transmitting and/or receiving on GPS and/or Bluetooth frequencies.

In an embodiment, the training device is configured to determine a physical activity performed by the user 90, and select a physiological algorithm based on the physical activity and the determination that the training device is used in the water environment. Therefore, the training device may determine that the user 90 is swimming, and use swimming as a basis for calculating energy expenditure, distance and/or speed, for example. The determination of the physical activity may be based on, for example, information from the motion circuitry and/or the determination that the training device is used in the water environment. For example, by using the information from the motion circuitry, training device may determine stroke rate of the user 90 when swimming. This may help selecting the physiological algorithm.

According to yet another embodiment, the apparatus carrying out the embodiments, such as the training device and/or electronics unit 330, comprises a circuitry including at least one processor and at least one memory including computer program code. When activated, the circuitry causes the apparatus to perform at least some of the functionalities according to any one of the embodiments, or operations thereof.

As used in this application, the term 'circuitry' refers to all of the following: (a) hardware-only circuit implementations, such as implementations in only analog and/or digital circuitry, and (b) combinations of circuits and soft-ware (and/or firmware), such as (as applicable): (i) a combination of processor(s) or (ii) portions of processor(s)/software including digital signal processor(s), software, and memory(ies) that work together to cause an apparatus to perform various functions, and (c) circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term 'circuitry' would also cover an implementation of merely a processor (or multiple processors) or a portion of a processor and its (or their) accompanying software and/or firmware. The term 'circuitry' would also cover, for example and if applicable to the particular element, a baseband integrated circuit or applications processor integrated circuit for a mobile phone or a similar integrated circuit in a server, a cellular network device, or another network device.

The techniques and methods described herein may be implemented by various means. For example, these techniques may be implemented in hardware (one or more devices), firmware (one or more devices), software (one or more modules), or combinations thereof. For a hardware implementation, the apparatus(es) of embodiments may be implemented within one or more application-specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. For firmware or software, the implementation can be carried out through modules of at least one chip set (e.g. procedures, functions, and so on) that perform the functions described herein. The software codes may be stored in a memory unit and executed by processors. The memory unit may be implemented within the processor or externally to the processor. In the latter case, it can be communicatively coupled to the processor via various means, as is known in the art. Additionally, the components of the systems described herein may be rearranged and/or complemented by additional components in order to facilitate the achievements of the various aspects, described with regard thereto, and they are not limited to the precise configurations set forth in the given figures, as will be appreciated by one skilled in the art.

Embodiments as described may also be carried out in the form of a computer process defined by a computer program. The computer program may be in source code form, object code form, or in some intermediate form, and it may be stored in some sort of carrier, which may be any entity or device capable of carrying the program. For example, the computer program may be stored on a computer program distribution medium readable by a computer or a processor. The computer program medium may be, for example but not limited to, a record medium, computer memory, read-only memory, electrical carrier signal, telecommunications signal, and software distribution package, for example. Coding of software for carrying out the embodiments as shown and described is well within the scope of a person of ordinary skill in the art.

Even though the invention has been described above with reference to an example according to the accompanying drawings, it is clear that the invention is not restricted thereto but can be modified in several ways within the scope of the appended claims. Therefore, all words and expressions should be interpreted broadly and they are intended to illustrate, not to restrict, the embodiment. It will be obvious to a person skilled in the art that, as technology advances, the inventive concept can be implemented in various ways. Further, it is clear to a person skilled in the art that the described embodiments may, but are not required to, be combined with other embodiments in various ways.

What is claimed is:

1. An electrode belt comprising:
   at least one electrode adapted to measure biometric signals related to heart activity of a user;
   a non-conductive strip having at least one opening, wherein the non-conductive strip comprises at least one fold such that at least two portions of the non-conductive strip are folded against each other, wherein a direction of the at least one fold is diverging compared to a longitudinal axis of the non-conductive strip, and wherein the at least one electrode is positioned between the folded at least two portions of the non-conductive strip so that the at least one electrode is enabled to be in physical contact with a skin of the user through the at least one opening; and
   a flexible strip to enable placement of the electrode belt against the skin of the user, wherein the non-conductive strip is coupled with the flexible strip such that, when in use, the at least one electrode is in physical contact with the skin of the user, wherein the non-conductive strip comprises two folds such that a first portion and a second portion of the non-conductive strip are folded against a third portion of the non-conductive strip, wherein the first portion is situated at a first end of the non-conductive strip and the second portion is situated at a second end of the non-conductive strip, wherein the third portion is situated between the first and the second portions, and wherein at least a first electrode of the at least one electrode is positioned between the first and the third portions and a second electrode of the at least one electrode is positioned between the second and the third portions, and wherein a first opening of the at least one opening is comprised in the first portion of the non-conductive strip and a second opening of the at least one opening is comprised in the second portion of the non-conductive strip.

2. The electrode belt of claim 1, wherein the at least one electrode is positioned between the folded two portions so that the at least one electrode is enabled to be in physical contact with the skin of the user through the at least one opening.

3. The electrode belt of claim 1, wherein the at least one electrode is encapsulated between the at least two portions so that the at least one electrode is at least partially visible through the at least one opening.

4. An electrode belt comprising:
   at least one electrode adapted to measure biometric signals related to heart activity of a user;
   a non-conductive strip having at least one opening, wherein the non-conductive strip comprises at least one fold such that at least two portions of the non-conductive strip are folded against each other, wherein a direction of the at least one fold is diverging compared to a longitudinal axis of the non-conductive strip, and wherein the at least one electrode is positioned between the folded at least two portions of the non-conductive strip so that the at least one electrode is enabled to be in physical contact with a skin of the user through the at least one opening; and
   a flexible strip to enable placement of the electrode belt against the skin of the user, wherein the non-conductive strip is coupled with the flexible strip such that, when in use, the at least one electrode is in physical contact with the skin of the user, wherein the non-conductive strip comprises two folds such that a first portion and a second portion of the non-conductive strip are folded against a third portion of the non-conductive strip, wherein the first portion is situated at a first end of the non-conductive strip and the second portion is situated at a second end of the non-conductive strip, wherein the third portion is situated between the first and the second portions, and wherein at least a first electrode of the at least one electrode is positioned between the first and the third portions and a second electrode of the at least one electrode is positioned between the second and the third portions, and wherein a first opening of the at least one opening is comprised in the first portion of the non-conductive strip and a second opening of the at least one opening is comprised in the second portion of the non-conductive, wherein the flexible strip comprises at least one fold such that at least two portions of the flexible strip are folded against each other, wherein the flexible strip comprises at least one opening, the non-conductive strip being positioned between the folded at least two portions of the flexible strip so that the at least one opening of the non-conductive strip and the at least one opening of the flexible strip are substantially aligned and against each other enabling the at least one electrode to be in contact with the skin of the user.

5. The electrode belt of claim 1, wherein the at least two portions of the flexible strip are attached together using an adhesive.

6. An electrode belt comprising:
   at least one electrode adapted to measure biometric signals related to heart activity of a user;
   a non-conductive strip having at least one opening, wherein the non-conductive strip comprises at least one fold such that at least two portions of the non-conductive strip are folded against each other, wherein a direction of the at least one fold is diverging compared to a longitudinal axis of the non-conductive strip, and wherein the at least one electrode is positioned between the folded at least two portions of the non-conductive strip so that the at least one electrode is enabled to be in physical contact with a skin of the user through the at least one opening;
   a flexible strip to enable placement of the electrode belt against the skin of the user, wherein the non-conductive strip is coupled with the flexible strip such that, when in use, the at least one electrode is in physical contact with the skin of the user, wherein the non-conductive strip comprises two folds such that a first portion and a second portion of the non-conductive strip are folded against a third portion of the non-conductive strip, wherein the first portion is situated at a first end of the non-conductive strip and the second portion is situated at a second end of the non-conductive strip, wherein the third portion is situated between the first and the second portions, and wherein at least a first electrode of the at least one electrode is positioned between the first and the third portions and a second electrode of the at least one electrode is positioned between the second and the third portions, and wherein a first opening of the at least one opening is comprised in the first portion of the non-conductive strip and a second opening of the at least one opening is comprised in the second portion of the non-conductive strip, further comprising:

at least one coupling member at least to enable electrical coupling of the at the at least one electrode with an electronics unit; and a holder unit at least to enable attachment of the electronics unit to the electrode belt, the holder unit comprising a cavity, wherein the electronics unit is configured at least to wirelessly transmit information related to heart activity received from the at least one electrode, wherein the holder unit is adapted and dimensioned to receive an enclosure of the electronics unit at least partially within the cavity.

7. The electrode belt of claim 6, wherein the non-conductive strip comprises at least one through-hole for the at least one coupling member, wherein the flexible strip comprises at least one through-hole for the at least one coupling member, and wherein the non-conductive strip is positioned to the flexible strip so that the at least one through-hole of the non-conductive strip and the at least one through-hole of the flexible strip are substantially aligned and against each other.

8. The electrode belt of claim 6, wherein the at least one coupling member reaches through at least one of an at least one through-hole of the non-conductive strip, the at least one through-hole of the flexible strip.

9. The electrode belt of claim 6, wherein the at least one coupling member is further adapted to enable attachment of the electronics unit to the electrode belt.

10. The electrode belt of claim 9, wherein the at least one coupling member comprises at least a first part of a snap fastener.

11. The electrode belt of claim 9, wherein the at least one coupling member comprises at least one hollow, and wherein an inner surface of the at least one hollow comprises at least one of a magnetic material, a material being magnetic when in a substantial magnetic field.

12. The electrode belt of claim 6, wherein the holder unit comprises the at least one coupling member.

13. The electrode belt of claim 6, wherein the electrode belt comprises the electronics unit, and wherein the electronics unit is configured at least to wirelessly transmit information related to heart activity received from the at least one electrode.

14. The electrode belt of claim 13, wherein at least one of the at least one coupling member, the holder unit enables detachable attachment of the electronics unit to the electrode belt.

15. The electrode belt of claim 13, wherein the electronics unit is further configured at least to perform operations comprising:
determining a change in an impedance of an antenna;
determining, based on the change in the impedance of the antenna, that the electronics unit is used in a water environment; and
selecting an operating mode based on the determining that the electronics unit is used in the water environment.

16. The electrode belt of claim 15, wherein the electronics unit is further configured at least to perform operations comprising:
determining a physical activity performed by the user; and
selecting a physiological algorithm based on the physical activity and the determination that the electronics unit is used in the water environment.

17. The electrode belt of claim 1, further comprising:
at least one fastening member enabling detachable attachment of the flexible strip against the body tissue of the user.

18. A method of manufacturing an electrode belt, the method comprising:
providing at least one electrode adapted to measure biometric signals related to heart activity of a user;
providing a non-conductive strip having at least one opening;
applying the at least one electrode on the non-conductive strip;
folding at least two portions of the non-conductive strip against each other, wherein the folding is performed to a direction that is divergent compared to a longitudinal axis of the non-conductive strip, and wherein the at least one electrode is positioned between the folded at least two portions of the non-conductive strip so that the at least one electrode is enabled to be in physical contact with a skin of the user through the at least one opening;
providing a flexible strip to enable placement of the electrode belt against the skin of the user; and
coupling the non-conductive strip to the flexible strip such that, when in use, the at least one electrode is in physical contact with the skin of the user, wherein the non-conductive strip comprises folds such that a first portion and a second portion of the non-conductive strip are folded against a third portion of the non-conductive strip, wherein the first portion is situated at a first end of the non-conductive strip and the second portion is situated at a second end of the non-conductive strip, wherein the third portion is situated between the first and the second portions, and wherein at least a first electrode of the at least one electrode is positioned between the first and the third portions and a second electrode of the at least one electrode is positioned between the second and the third portions, and wherein a first opening of the at least one opening is comprised in the first portion of the non-conductive strip and a second opening of the at least one opening is comprised in the second portion of the non-conductive strip, wherein the flexible strip comprises at least one fold such that at least two portions of the flexible strip are folded against each other, wherein the flexible strip comprises at least one opening, the non-conductive strip being positioned between the folded at least two portions of the flexible strip so that the at least one opening of the non-conductive strip and the at least one opening of the flexible strip are substantially aligned and against each other enabling the at least one electrode to be in contact with the skin of the user.

* * * * *